United States Patent [19]

Honda et al.

[11] 4,242,450

[45] Dec. 30, 1980

[54] METHOD OF HYDROLYZING SUGAR, PROTEIN OR THE LIKE AND APPARATUS THEREFOR

[75] Inventors: Yoshihiko Honda, Hidaka; Masanobu Koutake, Kodaira; Hidege Kanazawa, Kiyose; Taisuke Iwasaki, Hino; Shozo Ohba, Sayama; Honoh Hashiba, Tokorozawa; Gosei Kawanishi, Ichikawa, all of Japan

[73] Assignee: Snow Brand Milk Products Co., Ltd., Sapporo, Japan

[21] Appl. No.: 65,439

[22] Filed: Aug. 10, 1979

[30] Foreign Application Priority Data

Sep. 6, 1978 [JP] Japan ............................. 53-109260

[51] Int. Cl.$^3$ ..................... C12M 1/40; C12P 1/00
[52] U.S. Cl. ....................... 435/69; 435/41; 435/105; 435/262; 435/288
[58] Field of Search .................. 435/288, 41, 69, 105, 435/262

[56] References Cited

U.S. PATENT DOCUMENTS 3,767,535 10/1973 Havewala et al. ............... 435/41
3,809,613 5/1974 Vieth et al. ..................... 435/288

OTHER PUBLICATIONS

Vieth et al., "Design and Analysis of Immobilized-Enzyme Flow Reactors", in Applied Biochemistry & Bioengineering (Wingard et al.,Editors), vol. 1, pp. 221-234 (1976).

Pitcher, "Design and Operation of Immobilized Enzyme Reactors", in Advances in Biochemical Engineering, vol. 10, pp. 1 to 5 (1978).

Primary Examiner—Lionel M. Shapiro
Attorney, Agent, or Firm—Murray and Whisenhunt

[57] ABSTRACT

This method of hydrolyzing sugar, protein or the like and apparatus are advantageous especially in achieving the effective exhibition of the activity of immobilized enzymes, which method comprises jet-dispersing a constant-temperature aqueous solution containing a substrate such as sugar, protein or the like through an orifice and a net and making the same react in contact with a rotating immobilized enzyme.

14 Claims, 3 Drawing Figures

METHOD OF HYDROLYZING SUGAR, PROTEIN OR THE LIKE AND APPARATUS THEREFOR

BACKGROUND OF THE INVENTION

The present invention relates to a method of hydrolyzing a substrate such as sugar, protein or the like with an immobilized enzyme and an apparatus therefor.

DESCRIPTION OF THE PRIOR ART

Enzymes for use in hydrolysis (which is herein inclusive of "inversion") are generally immobilized for long-run repeated uses by enwrapping enzymes in water-insoluble substances such as cellulose triacetate, ion-exchange resin and the like, by adsorbing enzymes onto said substances or by bonding enzymes to said substances. The following reactors have hitherto been employed for the purpose of hydrolyzing the substrates with the above-enumerated immobilized enzymes:

(1) Ultrafiltrating membrane reactor, Combined CSTR/UF reactor,
(2) Stirred tank reactor,
(3) Packed-layer reactor, and
(4) Fluidized-bed reactor.

However, the reactor (1) or the process using the reactor is capable of treating colloid or insoluble substrates, but on the other hand is defective in that its capacity is deteriorated owing to the occurrence of concentration polarization and adsorption of enzyme protein on the film surface. The reactor (2) or the process using the reactor is surely capable of treating colloid or water insoluble substrate, but on the other hand is defective in that immobilized enzymes are liable to aggregate mutually into lumps and the recovery percentage of immobilized enzymes is inferior. The reactor (3) or the process using said reactor is generally said superior in reaction efficiency, but on the other hand is defective in that a "channelling" phenomenon (which means herein that a substrate-containing aqueous solution does flow through an immobilized enzyme not uniformly but only locally) is liable to take place and once it is caused, the reaction efficiency is rapidly lowered owing to the lowering of contacting rate between the immobilized enzyme and the aqueous solution. Furthermore, the immobilized enzyme after reaction can not easily be washed and dewatered the reactor (4) or the process using said reactor is superior in heat and mass transfer characteristics, but is deficient like (3) in that it is not so easy to wash and dewater the immobilized enzyme after reaction.

SUMMARY OF THE INVENTION

An object of the present invention is to provide a method of hydrolyzing sugar, protein or the like and an apparatus therefor which can not only draw the activity of immobilized enzymes efficiently but also enhance the after-treatment of immobilized enzymes, that is, washing and dewatering, as well as improve the recovery percentage of enzymes.

The hydrolyzing method according to the present invention is characterized by the steps of jet-dispersing through an orifice and a net a constant-temperature aqueous solution containing a substrate hydrolzsable with enzyme, and making the same react in contact with a rotating immobilized enzyme under the hydrolyzable conditions.

The hydrolyzing apparatus according to the present invention comprises a tank for maintaining at a constant temperature an aqueous solution containing a substrate hydrolyzable with enzymes, a rotary column rotating on a hollow shaft so that the solution may react in contact with an immobilized enzyme and a reaction container for accommodating column and stagnating the solution for a fixed period of time, wherein the shaft of the column is provided with a plurality of orifices which serve to jet the aqueous solution within the column, a net for uniformly dispersing the solution jetted through the orifices into the column is set on the outer periphery of the shaft, the column is partitioned into a plurality of chambers having partition walls for accommodating the immobilized enzyme dispersed to thereby prevent it from turning into large lumps, and a net for holding the immobilized enzyme is set on the outer periphery of the column.

In the present invention, it is preferred that the reaction system is circulated.

Suitable enzymes used in the present invention include lactose, glucose isomerase, amino acylase, amylase, gluco amylase, cellulose, pectinase, invertase, pepain, protease, catalose and the like. As the substrates treated suitably according to the present invention there can be enumerated, for instance in food industry, lactose, sucrose, starch, protein, cellulose and the like.

The immobilization of enzymes and microbes containing these enzymes is generally effected according to the following methods, for instance, of enwrapping enzymes in fibers when turning macro-molecules such as cellulose triacetate and the like into the fibers, combining enzymes with ion-exchange resins, for instance, such as ion-exchangeable cellulose, phenolformaldehyde resin and the like, chemically combining enzymes with a porous material such as porous glass, enwrapping enzymes in a fibrous material such as collagen, polyacrylamide or the like, etc.

The reaction condition for hydrolysis by enzymes considerably vary depending on kinds of substrates and enzymes. Generally speaking, however, the reaction is carried out under the following conditions; atmospheric pressure, a temperature in the range of from 5° to 70° C., and a pH value in the range of from 4 to 8. For instance, hydrolysis of lactose by lactose into glucose and galactose is suitably carried out under the conditions; a temperature in the range of from about 30° to 40° C. and a pH value in the range of from about 4.0 to 7.0. Suitably, inversion of D-glucose by glucose isomerase into fructose should be carried out under the conditions; a temperature in the range of from about 50° to 70° C. and a pH value in the range of about 6.5 to 8.5. The reaction conditions for hydrolyzing succrose by invertase into glucose and fructose suitably are a temperature of about 40° to 50° C. and a pH of about 5.0 to 8.0. Hydrolysis of starch by glucoamylase into glucose suitably should carried out at a temperature of about 40 to 50 and a pH of about 3 to 7. The conditions for hydrolyzing protein by protease into peptide and amino acid are a temperature of about 20° to 50° C. and a pH of about 3 to 10. The conditions for hydrolyzing cellulose by cellulose into glucose are a temperature of about 30° to 40° C. and a pH of about 5 to 7. The above-mentioned are conditions applied generally to free enzymes. In case the enzyme immobilized in or on insoluble maintenance are used in the apparatuses incorporated them therein, the condition suitable for each of them should be determined on taking into consideration the overall conditions such as the shape of apparatus, kind of substrate and so forth. In view of these hydrolysis reactions being influenced, above all, by temperature, control of temperature has much importance to the reactions.

The quantity of enzyme used varies depending on the reaction conditions such as the concentration of substrate, activity of enzyme, pH, temperature, etc. For instance, when lactose is used as substrate the suitable quantity of immobilized enzyme used (when dried) is 1/15 to 1/30 parts by weight per part by weight of substrate.

DESCRIPTION OF THE PREFERRED EMBODIMENTS

Figure 1:
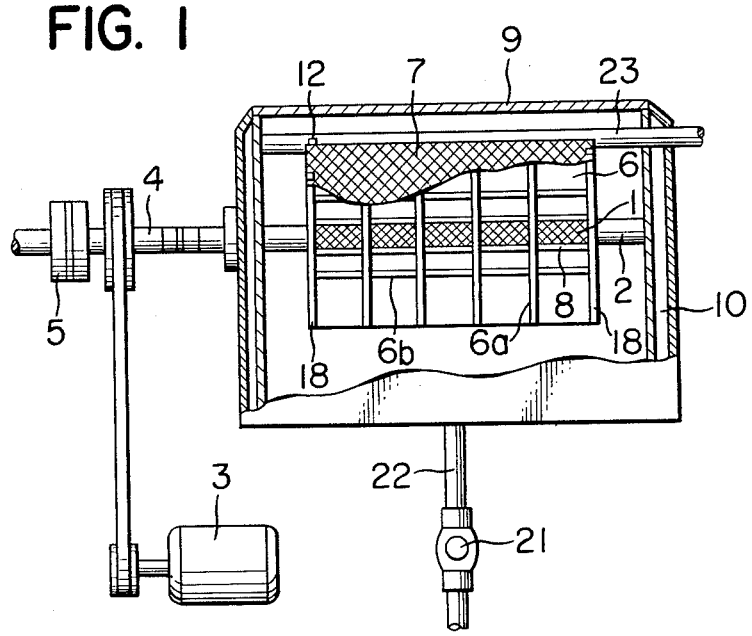
FIG. 1 is a partially cutaway front view of one embodiment of the apparatus, exclusive of a constant-temperature tank, according to the present invention.
Figure 2:
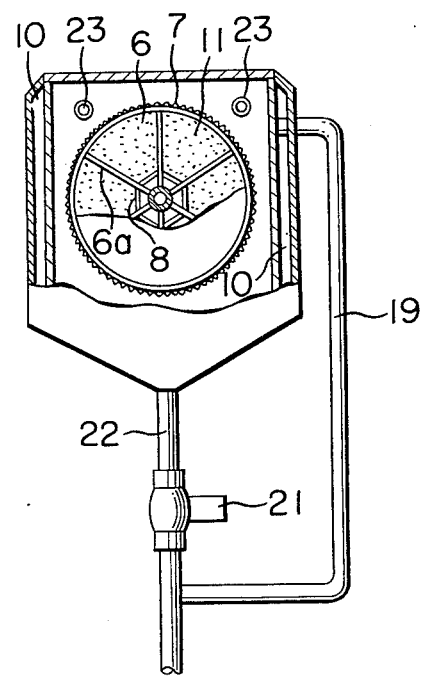
FIG. 2 is a side view of the same.

The apparatus according to the present invention will be explained with reference to the drawings hereinafter:

In FIG. 1 and FIG. 2, the apparatus illustrated therein comprises a hollow shaft (2) provided with a plurality of orifices (1), a speed change motor (3) for rotating said shaft (2), a packing box (5) for connecting the shaft (2) with a liquid supply pipe (4), a chamber (6) partitioned into plural chambers for accommodating an immobilized enzyme (11), a net (7) stretch-provided on the outer periphery of a column for holding the immobilized enzyme (11), a net (8) for dispersing the liquid sprayed through the orifices and allowing it to uniformly flow in the chambers (6) having accommodated the immobilized enzyme, a reaction container (9) for receiving a rotary column and stagnating the liquid for a fixed period of time, and a jacket (10) for cooling this container. The size of the dispersing net (8) is preferably about 50 to 80 meshes, while the size of the holding net (7) is preferably about 50 to 150 meshes.

The part in which the immobilized enzyme is charged and rotated, that is, the column consisting of the immobilized enzyme-accommodating chambers (6), net (7) and net (8) is called a rotary column. This column is received in the reaction container. The chambers (6) preferably should be defined so as to be radial-and square-shaped by radial partition wall (6a) and axial partition wall (6b). The liquid-dispersing net (8) defines the bottom of each chamber (6). The immobilized enzyme is charged into the chambers of the rotary column through the steps of charging a fixed quantity of immobilized enzyme uniformly into each chamber, thereafter setting the net (7) on the outer periphery of the rotary column and securing it to the side plate (18) of the rotary column by means of a bolt (12).

Figure 3:
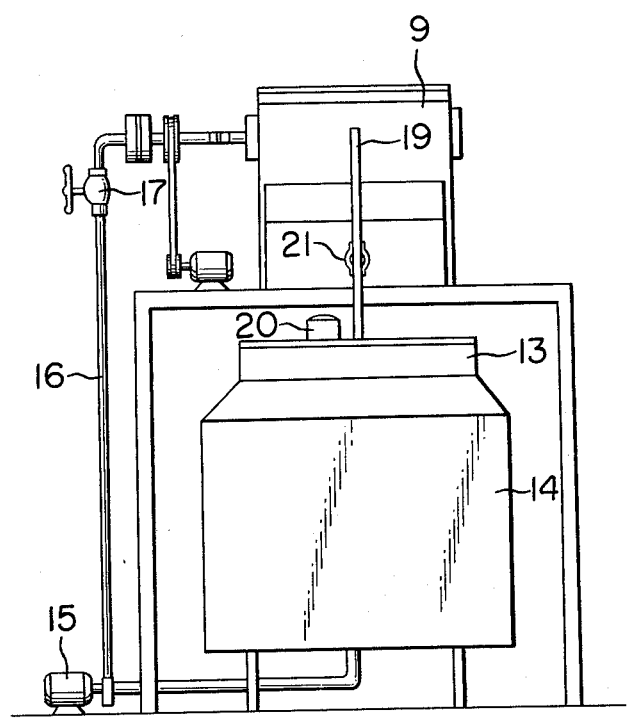
FIG. 3 is an elevational view of one embodiment of the whole apparatus according to the present invention.

The reason for having partitioned the rotary column into a number of chambers is to prevent the immobilized enzyme from turning into large lumps which act to decrease the contacting area between mobilized enzyme and liquid and thereby deteriorate the reaction efficiency. In FIG. 3, a substrate-containing aqueous liquid is supplied into a constant-temperature tank (13), cooled to a predetermined temperature by a cooling medium flowing within a jacket (14), for instance, water and then fed through a pump (15) and a pipe (16) to a reaction container (9). The flow rate is controlled by means of a valve (17).

The liquid fed to the reaction container provided with the temperature controlling jacket passes through the orifice (1) located on the hollow shaft (2), is dispersed by means of the net (8), and then is introduced into the immobilized enzyme-charged chamber. The specific substance contained in the liquid and contacted with the immobilized enzyme, for instance, such as sugar, protein or fat is hydrolyzed by each enzyme. The thus treated liquid is allowed to stagnate in the reaction container (9) for a fixed period of time and then is made flow down from an overflowing pipe (19) to the constant-temperature tank (13).

In the apparatus according to the present invention, the rotary column is rotated by means of the speed change motor (3) in order that the contacting degree between the immobilized enzyme and the liquid may be increased and thus the reaction efficiency may be raised, which additionally brings about the favorable result that the occurrence of channelling phenomenon can be prevented.

The partly hydrolyzed liquid returned to the constant-temperature tank (13) is stirred by means of a stirrer and is again fed into the reaction container (9) by the pump (15). It is necessary that the circulating flow rate of liquid and the number of rotations of the rotary column should be controlled depending on the relation of the quantities of immobilized enzyme and chamber capacity thereof. In other words, controlling of the flow rate depending on the relation of the quantities of immobilized enzyme and the chamber capacity is critical for the reaction to be conducted in a short period time and with good efficiency. In more detail, when the percentage of immobilized enzyme quantity for the chamber capacity is high, the circulating flow rate and the nubmer of rotations of the liquid is raised so that the contraflow of the liquid may be prevented which is caused by the fact that the immobilized enzyme is dense, thereby removing the stagnation of reaction substances on the surface of the immobilized enzyme and enhancing the reaction efficiently.

On the other hand, when the percentage of immobilized enzyme quantity is low, it is critical to prevent the liquid from flowing down without contacting with the immobilized enzyme by taking the following steps, that is, of reducing the circulating flow rate of the liquid so as to increase the residence time of the immobilized enzyme within the reactor and further reducing the number of rotations of the rotary column to such an extent that the immobilized enzyme charged in each chamber should not be omnipresent.

When it is required to achieve the hydrolysis reaction in a short period of time using the apparatus according to the present invention or the liquid to be treated reaches an excessive quantity, we should increase the quantity of immobilized enzyme and control the circulating flow rate of liquid and the number of rotations of the rotary column.

When the liquid reached a predetermined rate of reaction, the pump (15) is stopped and simultaneously the speed change motor (3) is stopped. Then, a drain valve (21) of the reaction container is opened so that the liquid within the reaction container (9) may flow down from a pipe (22) to the constant-temperature tank (13). Next, the reaction treated liquid within the constant-temperature tank (13) is drained, then the immobilized enzyme within the rotary column the constant temperature tank and the reaction container are washed. The constant-temperature tank may be washed using normal CIP, but the immobilized enzyme must be washed using ion-exchange water, buffer solution or the like. The solids attached to the surface of the immobilized enzyme are washed away by the ion-exchange water, buffer solution or the like sprayed out the orifice provided on the hollow shaft, and additionally the solids are washed away by them also through a shower nozzle (23) and the solids attached to the outside of the rotary column.

This reactor is such arranged that the supply of the washing solution such as ion-exchange water, buffer solution or the like is discontinued when it reaches a predetermined level of the container, and then the rotary column repeats its normal and reverse rotations for a fixed period of time, thereby achieving the result of washing the immobilized enzyme with high efficiency. After the passage of the fixed period of time, the drain valve is opened to discharge the soiled ion-exchange water, buffer solution or the like present within the reaction container. At this time, the rotary column is rotated at high speed so that the solids attached to the immobilized enzyme may be removed together with the ion-exchange water, buffer solution or the like. The repetition of aforesaid cycle several times can wash not only the immobilized enzyme completely but also the inside of the reaction container (9). These washing and dewatering operations can be effected automatically. The dewatered immobilized enzyme can be stored within the rotary column of the apparatus held at a fixed temperature. Therefore, there is no necessity of taking the immobilized enzyme, once charged, out of the rotary column so far as the immobilized enzyme is not deteriorated in its activity.

As is evident from the above explanation, the present invention eliminates the necessity of taking out the immobilized enzyme each time, whereby countermeasures for various contaminations resulting from taking the immobilized enzyme out of the apparatus may be dispensed with as well as every day operation may be simplified exceedingly. According to this figure, the apparatus is designed to dispose the reaction container above the constant-temperature tank and maintain the liquid surface uniformly by overflowing. On the other hand, it is also possible to dispose the reaction container at the same level with the constant-temperature tank by providing a level gage to the reaction container for the purpose of controlling a pump for returning the liquid from this container to the constant-temperature tank.

The apparatus referred to above includes the circulation system but it is to be noted that the aforesaid circulation system is not necessarily required in the case of the present invention.

Taking an instance, cellulose triacetate fibers enwrapped with lactase as immobilized enzyme are used and set in each chamber of the rotary column illustrated in FIG. 1 or FIG. 2. On the other hand, the solution of sterilized and then cooled skim milk is put in the constant-temperature tank illustrated in FIG. 3 and is maintained at a temperature of about 6° to 7° C.

Next, the circulating pump is started for feeding the solution to the rotary column, and the lactose is hydrolyzed under the following conditions:

Quantity of immobilized enzyme (total quantity, dry weight): 250–500 g (wherein the quantity of enzyme is 20–40 g)

Quantity of skim milk (skim milk concentration 10–13 wt.%); 200 l
Solution concentration (skim milk concentration): 8–15 wt.%
Solution temperature: 4°–10° C.
Solution pH: 6.5–7.5
Reaction time: 17–20 hours
Circulating flow rate: 0.5–1.5 $m^3$/hour As a result, there was obtained a final lactose hydrolysis rate ranging from 70 to 80%.

What is claimed is:

1. A method of hydrolyzing an enzyme hydrolyzable substrate which comprises jet-dispersing through an orifice and a net a constant-temperature aqueous solution containing a substrate hydrolyzable with enzyme and making the same react in contact with a rotating immobilized enzyme under the hydrolyzable conditions.

2. A method according to claim 1, wherein the size of the net is in the range of from 50 to 80 meshes.

3. A method according to claim 1, wherein the reaction system is circulated.

4. A method according to claim 1, wherein the reaction system is cooled.

5. A method according to claim 1, wherein the substrate is lactose and the enzyme is lactase.

6. A method according to claim 5, wherein the quantity of the substrate is in the range of from 15 to 30 parts by weight per part by weight of the immobilized enzyme when dried.

7. An apparatus for hydrolyzing an enzyme hydrolyzable substrate including a tank for maintaining at a constant temperature an aqueous solution containing a substrate hydrolyzable with enzymes, a rotary column rotating on a hollow shaft so that the solution may react in contact with an immobilized enzyme and a reaction container for accommodating the column and stagnating the solution for a fixed period of time, wherein the shaft of the column is provided with a plurality of orifices which serve to jet the aqueous solution within the column, a net for uniformly dispersing the solution jetted through the orifices into the column is set on the outer periphery of the shaft, the column is partitioned into a plurality of chambers with at least one partition wall for accommodating the immobilized enzyme dispersed to thereby prevent it from turning into large lumps, and a net for holding the immobilized enzyme is set on the outer periphery of the column.

8. An apparatus according to claim 7, wherein the size of the net set on the outer periphery of the shaft is in the range of from 50 to 150 meshes.

9. An apparatus according to claim 7, wherein the shaft of the rotary column is connected with the constant-temperature tank through the pump.

10. An apparatus according to claim 7, wherein the reaction container has a cooling jacket.

11. An apparatus according to claim 7, wherein the partition wall extends radially.

12. An apparatus according to claim 7, wherein the partition wall extends axially.

13. An apparatus according to claim 7, wherein partition walls extend in both radial and axial directions.

14. An apparatus according to claim 7, wherein the reaction container and the constant-temperature tank are connected through an overflow pipe.

* * * * *